United States Patent [19]

Jamison

[11] 3,962,431
[45] June 8, 1976

[54] INSECTICIDAL USE OF O,O-DIALKYL PHOSPHORODITHIOATE AND PHOSPHOROTHIOATE ESTERS OF OXAZOLIDINE-2,4-DIONE DERIVATIVES

[75] Inventor: Joel Dexter Jamison, Mountainside, N.J.

[73] Assignee: Hercules Incorporated, Wilmington, Del.

[22] Filed: Apr. 26, 1972

[21] Appl. No.: 247,750

Related U.S. Application Data

[60] Continuation-in-part of Ser. No. 115,735, Feb. 16, 1971, abandoned, which is a division of Ser. No. 694,813, Jan. 2, 1968, Pat. No. 3,632,598.

[52] U.S. Cl. .................................. 424/200; 424/23
[51] Int. Cl.$^2$ .................................. A01N 9/36
[58] Field of Search .................................. 424/200

[56] References Cited
UNITED STATES PATENTS

| | | |
|---|---|---|
| 3,406,179 | 10/1968 | Jamison .............................. 424/200 |
| 3,440,247 | 4/1969 | Dorer, Jr. ........................ 424/200 X |

*Primary Examiner*—Dale R. Ore
*Attorney, Agent, or Firm*—George H. Hopkins

[57] ABSTRACT

Disclosed is the use of compounds of the formula:

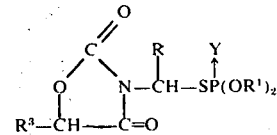

in which Y is O or S, $R^1$ is $CH_3$ or $C_2H_5$, $R^2$ and $R^3$ are H or $CH_3$. These compounds are particularly effective systemically against the two-spotted mite.

7 Claims, No Drawings

INSECTICIDAL USE OF O,O-DIALKYL PHOSPHORODITHIOATE AND PHOSPHOROTHIOATE ESTERS OF OXAZOLIDINE-2,4-DIONE DERIVATIVES

The application is a continuation-in-part of application Ser. No. 115,735, filed Feb. 16, 1971, now abandoned as a division of the application Ser. No. 694,813, filed Jan. 2, 1968, on which U.S. Pat. No. 3,632,598 was granted.

This invention relates to organophosphorous compounds containing a 2,4-oxazolidinedione ring system, and to insecticidal composition containing the same.

In accordance with this invention, it has been found that compounds of the formula

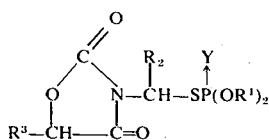

where Y is O or S, $R^1$ is $CH_3$ or $C_2H_5$, and $R^2$ and $R^3$ are individually H or $CH_3$ are highly toxic by systemic action to the two-spotted mite.

The compounds of this invention are readily absorbed by plants through the root system and, in many cases, also through the foliage, and they are transported through the plant to the growing tips where the toxicity is exerted on insects which attack the plant.

In practicing the invention, effective quantities of the toxic compounds are placed in the locus of the roots for absorption through the roots, or on the foliage for absorption through the foliage. The toxic compounds are used in compositions in admixture with a granular solid carrier or a wettable powder or as an aqueous emulsion of the compound itself or of the compound dissolved in an organic solvent or adsorbed on a wettable powder. The composition of the toxic compound adsorbed on a granular solid is used when applied along with seeds at planting. The granular solid and seeds are then planted together as a mixture. The toxic compound may also be applied to the seeds themselves as a wettable powder, as an aqueous emulsion, or as an organic solvent solution so that the toxic compound is placed in the locus of the roots by planting of the seeds. The toxic compounds can also be added to the soil after the plants to be protected have sprouted by directing an aqueous emulsion of the toxic compound with or without a solid carrier to the locus of the roots in the soil, and the toxic compound will be carried into the soil with rain or artificial watering.

The toxic compounds are alternatively applied to the foliage as an aqueous emulsion, with or without a solid carrier, when treatment is made when the plants are in the foliage stage of growth.

The methods of using systemic insecticides are well known in the art.

The compounds of this invention preferably are made available to applicators as dispersible concentrates of the toxic compound and a dispersing agent. The dispersing agent is a solid inorganic surface active agent which is itself finely divided, or is a dispersible aggregate of finely divided particles, or is an organic surface active agent. The inorganic surface active agents include talc, attapulgite, pyrophylite, diatomaceous earth, kaolin, aluminum and magnesium silicates, montmorillonite and other clays, fuller's earth and their equivalents. Suitable organic surface active agents are anionic, cationic or non-ionic surface active agents. These include alkali metal (sodium or potassium) oleates and similar soaps, amine salts of long chain fatty acids (oleates), sulfonated animal and vegetable oils (fish oils and castor oil), sulfonated petroleum oils, sulfonated acyclic hydrocarbons; sodium salts of lignin sulfonic acids, sodium alkylnaphthalene sulfonates, sodium lauryl sulfonate, disodium monolauryl phosphates; sorbitol laurate, pentaerythritol monostearate, glycerol monostearate, polyethylene oxides; ethylene oxide condensates of stearic acid, stearyl alcohol, stearyl amine, rosin amine, dehydroabietyl amine, glycerol monolaurate and the like; lauryl amine salts, dehydroabietyl amine salts, lauryl pyridinium bromide, stearyltrimethylammonium bromide and cetyldimethylbenzylammonium chloride.

When the dispersing agent comprises an inorganic surface active agent, an organic surface active agent is often used with it to produce a wettable powder.

When the dispersing agent comprises an organic surface active agent, an organic solvent is often included in an amount necessary to produce a homogeneous fluid solution which is readily pourable. The organic solvent is one which dissolves both the toxicant and the surface active agent. Such solvents include low molecular weight alcohols, acetone, methyl ethyl ketone, toluene, xylenes and petroleum distillates.

The toxicants are preferably compounded in the form of water dispersible concentrates which contain 10–50% by weight toxicant and 50–90% by weight dispersing agent, wherein the dispersing agent comprises either 20–100% by weight organic surface active agent, and up to 80% by weight organic solvent in which the surface active agent is soluble or, in the case where the concentrate is a wettable powder, the dispersing agent comprises 50–100% by weight of a solid inorganic surface active agent, and up to 50% by weight organic surface active agent.

The emulsifiable concentrate is usually diluted with water to form an aqueous emulsion having an effective toxicant concentration, for example 0.0005–5% by weight, and this is sprayed on the locus of the roots or foliage of the plants to be protected.

The compounds of this invention are made as disclosed in U.S. Pat. No. 3,632,598.

The preparation of the compounds of this invention is illustrated by the following examples in which all percentages are by weight.

EXAMPLE 1

A mixture of 17.2 g. of 2,4-oxazolidinedione, 6.0 g. paraformaldehyde and 0.1 g. $Ba(OH)_2$ was melted and heated at 90°C. for one hour. The melt was taken into methylene chloride (100 ml.) and treated with 36 g. phosphorous pentachloride. The mixture was let stand overnight at 25°C. and the solvent removed. The residue was treated with cold water and recrystallized from isopropanol to give 16.3 g. of 3-chloromethyl-2,4-oxazolidinedione; m.p. 68°–69°C., which analyzed 23.7% chlorine (theory: 22.7%).

A mixture of 7.5 g. 3-chloromethyl-2,4-oxazolidinedione and 9.6 g. ammonium O,O-dimethyl phosphorodithioate in 40 ml. of water was heated at 40°–50°C. for 8 hours. The organic layer was taken up in benzene and washed with 5% aqueous sodium bicarbonate and water and then dried. On removal of the solvent, there remained 12.2 g. O,O-dimethyl S-(2,4-oxazolidinedione-3-yl) methyl phosphorodithioate as a colorless oil which analyzed 11.5% P. (11.4% P., theory).

EXAMPLE 2

Following the procedure of Example 1, 11.8 g. of ammonium O,O-diethyl phosphorodithioate was reacted with 7.5 g. 3-chloromethyl-2,4-oxazolidinedione, and 14.4 g. O,O-diethyl S-(2,4-oxazolidinedione-3-yl) methyl phosphorodithioate was recovered as a colorless oil which analyzed 9.8% P (10.3% P., theory).

EXAMPLE 3

Following the procedure of Example 1, 12.3 g. of 3-chloromethyl-5-methyl-2,4-oxazolidinedione prepared in an analogous manner was reacted with 14.4 g. ammonium O,O-dimethyl phosphorodithioate, and 17.4 g. O,O-dimethyl S-(5-methyl-2,4-oxazolidinedione-3-yl) methyl phosphorodithioate was recovered as an oil which analyzed 11.2% P. (10.9% P., theory).

EXAMPLE 4

Following the procedure of Example 1, 12.3 g. of 3-chloromethyl-5-methyl-2,4-oxazolidinedione prepared in analogous manner was reacted with 17.6 g. of ammonium O,O-diethyl phosphorodithioate and 18.8 g. O,O-diethyl S-(5-methyl-2,4-oxazolidinedione-3-yl) methyl phosphorodithioate was obtained as an oil which analyzed 9.9% P. (9.1% P., theory).

EXAMPLE 5

3-Vinyl-5-methyl-2,4-oxazolidinedione was prepared from 5-methyl-2,4-oxazolidinedione by the procedure for making 3-vinyl-2,4-oxazolidinedione in Example 9 hereinafter.

A solution of 11.5 g. of O,O-dimethyl phosphorodithioic acid and 8.4 g. 3-vinyl-5-methyl-2,4-oxazolidinedione in 50 ml. benzene was heated at 50°C. for 3 hours, and the benzene was distilled off with final heating for 3 hours at 90°C. The product was redissolved in benzene, washed with 5% aqueous sodium bicarbonate and water and dried. On removal of the benzene, there remained 15.3 g. O,O-dimethyl S-[1-(5'-methyl-2',4'-oxazolidinedione-3'-yl) ethyl] phosphorodithioate which was an oil analyzing 11.2% P. (10.4% P., theory).

EXAMPLE 6

Following the procedure of Example 5, 13.5 g. O,O-diethyl phosphorodithioic acid was reacted with 8.4 g. 3-vinyl-5-methyl-2,4-oxazolidinedione and 17.5 g. O,O-diethyl S-[1-(5'-methyl-2',4'-oxazolidinedione-3'-yl) ethyl] phosphorodithioate which was an oil analyzing 9.9% P. (9.5% P., theory) was obtained.

EXAMPLE 7

A mixture of 20.2 g. of 2,4-oxazolidinedione, 6.6 g. of paraformaldehyde and 0.1 g. Ba(OH)$_2$ was melted and heated at 90°C. for one hour. The melt was taken into 100 ml. methylene chloride and 18.2 g. phosphorous tribromide added at 0°–10°C. The mixture was let stand at 25°C. overnight, the methylene chloride solution decanted and the solvent removed. The residue was washed with water and recrystallized to give 16.7 g. of 3-bromomethyl-2,4-oxazolidinedione; m.p. 63°–64°C. An NMR spectrum was consistent with its structure.

A mixture of 15.0 g. 3-bromomethyl-2,4-oxazolidinedione and 13.0 g. ammonium O,O-dimethyl phosphorothioate in 100 ml. acetonitrile was heated at 25°C. for 48 hours, and at 60°C. for 4 hours. The mixture was filtered, the acetonitrile was distilled off, and the residue was dissolved in methylene chloride. The methylene chloride solution was filtered, and the filtrate was freed of solvent by heating under reduced pressure. The residue from this treatment was 15.3 g. O,O-dimethyl S-(2,4-oxazolidinedione-3-yl) methyl phosphorothioate which analyzed 12.6% P. (12.2% P., theory).

EXAMPLE 8

A mixture of 15.0 g. 3-chloromethyl-2,4-oxazolidinedione and 20.4 g. ammonium O,O-diethyl phosphorothioate in 100 ml. dimethyl sulfoxide was heated at 25°C. for 48 hours, and at 60°C. for 3 hours. The mixture was diluted with 400 ml. water, and extracted with methylene chloride. The methylene chloride extract was dried and freed of solvent to obtain 18.3 g. O,O-diethyl S-(2,4-oxazolidinedione-3-yl) methyl phosphorothioate which analyzed 11.1% P. (10.9% P., theory).

EXAMPLE 9

A mixture of 202 g. of 2,4-oxazolidinedione, 185 g. of ethylene carbonate and 1.0 g. of sodium bicarbonate was heated to 155°–160°C. for three hours. The melt was cooled, dissolved in 500 ml. pyridine and treated with 220 g. of acetic anhydride. This mixture was heated to 100°C. for three hours, the pyridine removed and the residue distilled at 3–8 mm. Hg pressure to give 148.0 g. 3-(2'-acetoxyethyl)-2,4-oxazolidinedione, b.p. 144°–150°C., which analyzed 7.8% nitrogen (theory: 7.5%).

This acetate was added to a tube packed with stainless steel helices which was heated to 580°C. The pyrolyzate was distilled to give 51.1 g. 3-vinyl-2,4-oxazolidinedione, b.p. 100°–105°C./0.2 mm., which analyzed 10.8% nitrogen (theory: 10.8%).

A mixture of 17.0 g. of O,O-dimethyl phosphorodithioic acid and 8.4 g. 3-vinyl-2,4-oxazolidinedione was heated at 90°C. for 8 hours. The product was dissolved in benzene, washed with 5% aqueous sodium bicarbonate and water and dried. On removal of the benzene, there remained 14.2 g. O,O-dimethyl S-[1-(2',4'-oxazolidinedione-3'-yl) ethyl] phosphorodithioate which was an oil analyzing 10.4% P. (10.9% P., theory).

EXAMPLE 10

Following the procedure of Example 9, 20.0 g. O,O-diethyl phosphorodithioic acid was reacted with 9.0 g. 3-vinyl-2,4-oxazolidinedione and 21.9 g. O,O-diethyl S-[1-(2',4'-oxazolidinedione-3'-yl) ethyl] phosphorodithioate which was an oil analyzing 10.6% P. (9.9% P., theory) was obtained.

Each of the compounds of the above examples was made into a concentrate by dissolving 1.5 g. of the toxicant compound in 1 ml. toluene to which was added 1 ml. Tween 20 sorbitol monolaurate polyoxyethylene derivative. This concentrate was then dispersed in 150 ml. water to produce an emulsion containing the toxicant at 1% by weight, and emulsions of lower concentrations were produced by diluting aliquots of this emulsion with the required amount of water.

The emulsions were then tested against various insects, including two-spotted mites, systemically - (TSM-S).

Two-Spotted Mite, Systemic - Lima bean rooted seedlings (5 to 6 days old) which have been grown under test conditions are removed from the soil, and the roots are placed in culture tubes containing emulsions of the toxicant at various concentrations. After 24 hours, 50–100 two-spotted mites are placed on the leaves of one such seedling. These tests are carried out at 78°F. and 50% relative humidity. The mortality of mites is determined after 6 days.

The results of the testing are set forth in Table 1.

Table 1

Toxicity to Insects of Compounds of the Formula

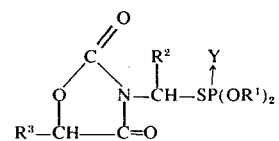

| Example | $R^1$ | $R^2$ | $R^3$ | Y | TSM-S %/p.p.m. |
|---|---|---|---|---|---|
| 1 | $CH_3$ | H | H | S | 100/10 |
| 2 | Et | H | H | S | 100/50 |
| 3 | $CH_3$ | H | $CH_3$ | S | 100/10 |
| 4 | Et | H | $CH_3$ | S | 40/50 |
| 5 | $CH_3$ | $CH_3$ | $CH_3$ | S | 100/50 |
| 6 | Et | $CH_3$ | $CH_3$ | S | 80/50 |
| 7 | $CH_3$ | H | H | O | 100/50 |
| 8 | Et | H | H | O | 100/50 |
| 9 | $CH_3$ | $CH_3$ | H | S | 100/50 |
| 10 | Et | $CH_3$ | H | S | 100/50 |

Tests were also carried out on potted lima bean seedlings in which the toxicants were applied to the roots as aqueous emulsions and to foliage as aqueous emulsions, and were found to be effective. Sowing clay granules containing adsorbed toxicant compounds of this invention at the rate of ½ pound of toxicant compound per acre along with pea seeds or cotton seeds has been found effective in further tests as shown by toxicity of the plants after sprouting to aphids and other sucking insects.

The compounds of this invention are all highly toxic to the two-spotted mite specifically, but they are also toxic to other sucking insects such as mites. Their toxicity as contact insecticides is selective and variable with the compounds used. Their common utility is thus that of a systemic insecticide and in addition they have high toxicity to a wide variety of insects such that mixtures of methyl and ethyl esters, for example, are useful as broad spectrum contact insecticides as well as systemic insecticides.

I claim:

1. An insecticidal composition comprising an insecticidally effective quantity of a compound of the formula:

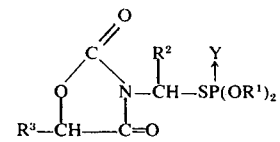

in which Y is O or S; $R^1$ is $CH_3$ or $C_2H_5$; and $R^2$ and $R^3$ are $CH_3$ or H, and a dispersing agent therefor.

2. A water dispersible concentrate according to claim 1 in which said compound is at a concentration of 10–50% by weight, and said dispersing agent is at a concentration of 50–90% by weight.

3. A water dispersible composition according to claim 2 in which the dispersing agent comprises an inorganic solid finely-divided surface-active agent.

4. A water dispersible composition according to claim 3 in which the dispersing agent comprises an organic surface-active agent.

5. A water dispersible composition according to claim 4 in which the dispersing agent also comprises organic solvent, and said compound and said organic surface-active agent are dissolved in said solvent.

6. A process for the control of an insect, which comprises contacting said insect with an insecticidally effective quantity of a compound of the formula:

in which Y is O or S; $R^1$ is $CH_3$ or $C_2H_5$; and $R^2$ and $R^3$ are $CH_3$ or H.

7. A process according to claim 6 in which said insect is a sucking insect.

* * * * *